US008626286B2

(12) United States Patent
Yamaguchi et al.

(10) Patent No.: US 8,626,286 B2
(45) Date of Patent: Jan. 7, 2014

(54) ANALYZING WAVES OF ELECTROCARDIOGRAM DURING CPR USING FOURIER SERIES AND OPTIMIZATION STRATEGIES

(75) Inventors: Yoshihiro Yamaguchi, Tokyo (JP); Hidetoshi Oya, Kawasaki (JP)

(73) Assignee: CAE Solutions Corporation, Tokyo (JP)

( * ) Notice: Subject to any disclaimer, the term of this patent is extended or adjusted under 35 U.S.C. 154(b) by 107 days.

(21) Appl. No.: 13/282,440

(22) Filed: Oct. 26, 2011

(65) Prior Publication Data

US 2012/0041327 A1 Feb. 16, 2012

Related U.S. Application Data

(63) Continuation of application No. 12/342,178, filed on Dec. 23, 2008, now Pat. No. 8,190,255.

(30) Foreign Application Priority Data

Dec. 27, 2007 (JP) .................................. 2007-337193

(51) Int. Cl.
*A61N 1/18* (2006.01)
*A61N 1/39* (2006.01)
*A61B 5/0428* (2006.01)

(52) U.S. Cl.
CPC ............ *A61N 1/3925* (2013.01); *A61B 5/0428* (2013.01); *Y10S 128/901* (2013.01)
USPC .............................................. 607/6; 128/901

(58) Field of Classification Search
USPC ........... 607/4–7; 128/901; 600/508–510, 513, 600/515–519, 521, 523; 601/41
See application file for complete search history.

(56) References Cited

U.S. PATENT DOCUMENTS 6,287,328 B1 * 9/2001 Snyder et al. ................. 600/509
7,171,269 B1 1/2007 Addison et al.

(Continued)

FOREIGN PATENT DOCUMENTS

| EP | 1 769 737 | 4/2007 |
| JP | 2007-020878 | 2/2007 |
| JP | 2007-117481 | 5/2007 |
| WO | WO 01/82099 | 11/2001 |
| WO | WO 2006/016289 | 2/2006 |

OTHER PUBLICATIONS

Berger, Ronald D., et al. ("Rhythm discrimination during uninterrupted CPR using motion artifact reduction system" Resuscitation. 75.1 (2007); 145-152).*
Rheinberger, Klaus, et. al. ("Removal of CPR Artifacts From Ventricular Fibrillation ECG by Adaptive Regression on Lagged Reference Signals" IEEE Transactions on Biomedical Engineering. 55.1 (2008); 130-137).*
Search Report in European Patent Application No. 0802257.3-1265, mailed Apr. 6, 2009.

*Primary Examiner* — Carl H Layno
*Assistant Examiner* — Jessica Anthony
(74) *Attorney, Agent, or Firm* — Brundidge & Stanger, P.C.

(57) ABSTRACT

Electrocardiogram wave data in which a component of cardiac massage is removed from the electrocardiogram wave data is generated, so that the electrocardiogram wave at the time of cardiopulmonary resuscitation is identified. An electrocardiogram wave processing system of obtaining and processing the electrocardiogram wave data includes a wave identification unit that identifies an electrocardiogram wave from the obtained electrocardiogram wave data, a feature selection unit that selects a feature pattern including a feature when a cardiac massage has been performed with respect to the electrocardiogram wave data identified by the wave identification unit, a generation unit that generates a component of the cardiac massage using the feature pattern selected by the feature selection unit, and a removal unit that removes, from the obtained electrocardiogram wave data, the component of the cardiac massage generated by the generation unit.

11 Claims, 14 Drawing Sheets

(56) References Cited

U.S. PATENT DOCUMENTS

| | | |
|---|---|---|
| 8,190,255 B2 * | 5/2012 | Yamaguchi et al. ............. 607/6 |
| 2001/0056245 A1 | 12/2001 | Mylnash et al. |
| 2004/0059237 A1 | 3/2004 | Narayan et al. |
| 2005/0101889 A1 * | 5/2005 | Freeman et al. ................ 601/41 |
| 2005/0256415 A1 | 11/2005 | Tan et al. |
| 2006/0025825 A1 * | 2/2006 | Bowers ............................ 607/5 |
| 2006/0149157 A1 * | 7/2006 | Weil et al. .................... 600/518 |

* cited by examiner

F I G . 2
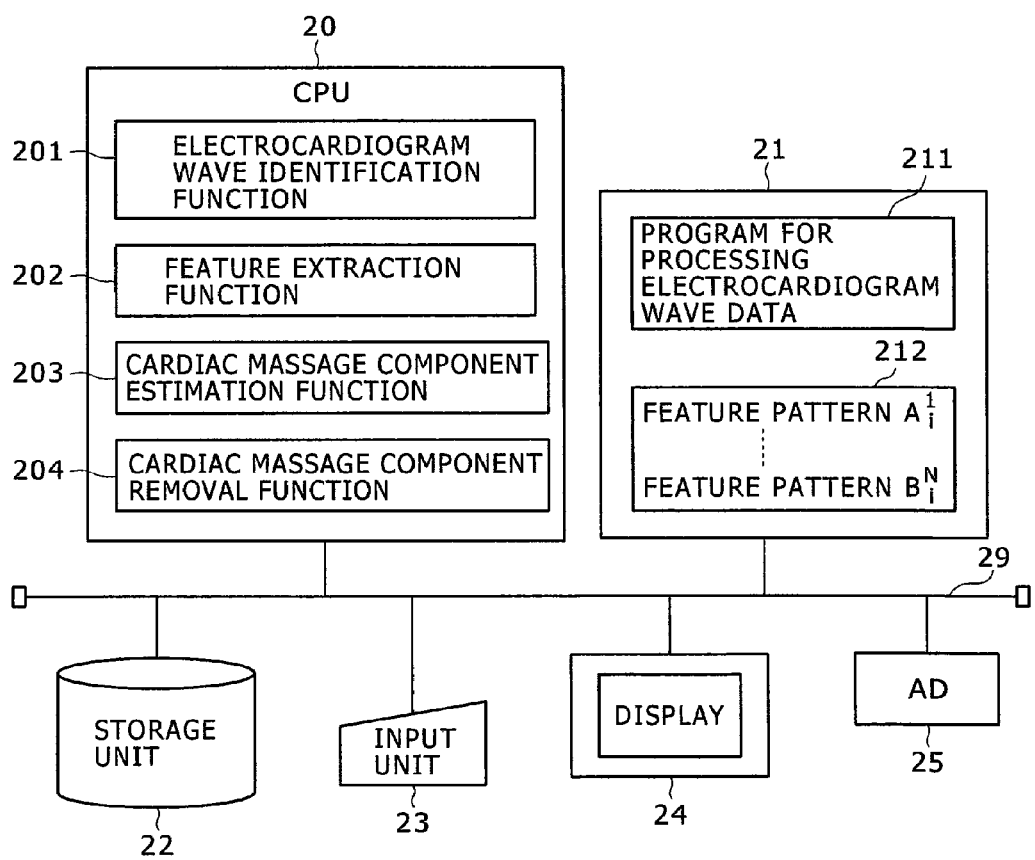

ANALYZING WAVES OF ELECTROCARDIOGRAM DURING CPR USING FOURIER SERIES AND OPTIMIZATION STRATEGIES

This application is a continuation application of U.S. application Ser. No. 12/342,178 filed on Dec. 23, 2008, now U.S. Pat. No. 8,190,255, the entirety of which is incorporated herein by reference.

BACKGROUND OF THE INVENTION

1. Priority Application

This application claims the benefit of priority from Japanese Patent 2007-337193, filed Dec. 27, 2007, the disclosure of which also is entirely incorporated herein by reference.

2. Field of the Invention

The present invention relates to a system and a method for analyzing waves of electrocardiogram, and in particular, to a system and a method for analyzing waves of electrocardiogram at the time of cardiopulmonary resuscitation, and a program executed on a computer for analyzing the waves of electrocardiogram.

3. Description of the Related Art

In most cases, sudden cardiac arrest is caused by severe arrhythmia such as Ventricular Fibrillation (VF), and the use of defibrillation (electrical defibrillation) as soon as possible is effective against the severe arrhythmia. In addition, according to the American Heart Association (AHA)'s guideline providing a standard guideline of the cardiopulmonary resuscitation law, a continuous cardiac massage is an important basic concept.

In order to determine whether the electrocardiogram waves need to be subjected to defibrillation, all cardiopulmonary resuscitations must be stopped. However, this stop contradicts the continuous cardiac massage. In addition, stopping the cardiopulmonary resuscitations for the moment causes a critical adverse effect on a recovery of a patient. Further, stopping the cardiopulmonary resuscitation for 10 seconds or more damages the brain, which also becomes the cause of sequela.

Several techniques are proposed for analyzing electrocardiogram wave data. For example, according to JP-A-2007-117481, a monitor system is disclosed for measuring an electrocardiogram and fluctuation of a baseline of the electrocardiogram to monitor both of the heart condition and the psychological disturbance.

In addition, according to JP-A-2007-20878, a noise elimination apparatus is proposed, which employs a morphology filter to eliminate the baseline fluctuation noise of which the frequency component included in the electrocardiogram wave signal is 0.5 Hz or less.

When the electrocardiogram waves are identified and processed at the time of cardiopulmonary resuscitation, a system is desperately required which can recognize waves to which the defibrillation must be applied in a safe and secure way while taking various resuscitation measures including a continuous cardiac massage. The implementation of the system is expected to bring a significant effect on resuscitation rate enhancement of the heart arrest patient.

In addition, neither JP-A-2007-117481 nor JP-A-2007-20878 mentioned above discloses or suggests how to identify the electrocardiogram waves at the time of cardiopulmonary resuscitation. Further, a technique of analyzing the electrocardiogram waves obtained during the cardiac massage and determining whether the defibrillation must be applied to the electrocardiogram waves is not disclosed at all.

SUMMARY OF THE INVENTION

An object of the invention is therefore to provide a system, a method, and a program for analyzing waves of electrocardiogram at the time of cardiopulmonary resuscitation.

Another object of the invention is to provide a system, a method, and a program, which can generate electrocardiogram waves in which components generated by a cardiac massage are removed from electrocardiogram wave data obtained during a continuous cardiac massage and can be used for identifying the electrocardiogram waves.

Another object of the invention is to perform analysis using a frequency component of obtained electrocardiogram wave data and to determine whether defibrillation must be applied to the electrocardiogram wave data based on the analysis result.

The present invention can identify electrocardiogram wave data obtained during a continuous cardiac massage, select a feature pattern from the identified electrocardiogram wave data, generate a component of the cardiac massage from the identified feature pattern, and remove the generated cardiac massage component from the original electrocardiogram wave data.

According to a first aspect of the invention, there is provided a system of analyzing electrocardiogram wave data obtained from a subject, the system including: a wave identification unit that identifies an electrocardiogram wave from the obtained electrocardiogram wave data; a feature selection unit that selects a feature pattern including a feature when a cardiac massage has been performed with respect to the electrocardiogram wave data identified by the wave identification unit; a generation unit that generates a component of the cardiac massage using the feature pattern selected by the feature selection unit; and a removal unit that removes, from the obtained electrocardiogram wave data, the component of the cardiac massage generated by the generation unit.

Preferably, when a Fourier series expansion is expressed by the expression 3:

$$y(t) = a_0 + \sum_{i=1}^{\infty} \left( a_i \cos \frac{2\pi i t}{T} + b_i \sin \frac{2\pi i t}{T} \right)$$

and an approximate wave of the Fourier series expansion is expressed by the expression 4:

$$\hat{y}(t) = \alpha_0 + \sum_{i=1}^{M} \left( \alpha_i \cos \frac{2\pi i t}{T} + \beta_i \sin \frac{2\pi i t}{T} \right)$$

assuming that the obtained electrocardiogram wave data is a wave in which a fundamental wave component and a harmonic wave component overlap each other, errors of $\hat{y}(t)$ and $y(t)$ are made to be as small as possible by adjusting $\alpha=(\alpha_0, \alpha_1, \alpha_2, \alpha_3, \ldots)$ and $\beta=(\beta_1, \beta_2, \beta_2, \ldots)$, thereby searching $\alpha$ and $\beta$.

In addition, preferably, the system further includes a storage unit that store plural different feature patterns (referred to as registration feature patterns) in advance, wherein the feature selection unit refers to the registration feature patterns stored in the storage unit to select the registration feature pattern that is the most similar to the feature pattern included in the electrocardiogram wave data identified by the wave identification unit.

In addition, preferably, the electrocardiogram wave data includes a wave of which the feature when the cardiac massage has been performed is represented as an amplitude component, the storage unit stores the registration feature patterns configured using a normalization distribution and thresholds that have been statistically collected, including, as the amplitude component, the feature when the cardiac massage has been performed, and the feature selection unit extracts the amplitude component from the electrocardiogram wave data identified by the wave identification unit, and also cross-checks the extracted amplitude component with amplitude components of the registration feature patterns stored in the storage unit to select the registration feature pattern of which the amplitude component is the most similar to amplitude component of the extracted amplitude component.

In addition, preferably, the feature selection unit mainly uses a wave having an amplitude component ranging from 1.5 Hz to 1.9 Hz.

In addition, preferably, the generation unit multiplies a normalized value of the selected feature pattern by a weighted value with respect to the electrocardiogram wave data identified by the wave identification unit.

In addition, preferably, the removal unit mainly removes, from the electrocardiogram wave data, the component of the cardiac massage of which the electrocardiogram wave data has the amplitude component ranging from 1.5 Hz to 1.9 Hz.

In addition, preferably, the system further includes a display that displays an electrocardiogram wave (a second electrocardiogram wave) output from the removal unit of which the component of the cardiac massage is removed.

In addition, preferably, the system further includes a processing unit that executes a computer program, wherein the computer program for implementing each function of the wave identification unit, the feature selection unit, the generation unit, and the removal unit is executed on the processing unit.

In addition, preferably, the system further includes determination means for determining whether defibrillation needs to be applied to the subject by cross-checking the electrocardiogram wave output from the removal unit with predetermined wave information already prepared in the storage unit, and alarm means for raising an alarm by means of voice or display upon determination of the determination unit that the defibrillation needs to be applied to the subject.

According to a second aspect of the invention, there is provided a method of obtaining and analyzing electrocardiogram wave data using a processing apparatus, the method including: identifying electrocardiogram wave data (first electrocardiogram wave data) when a cardiac massage has been performed from the obtained electrocardiogram wave data; selecting a feature pattern from the identified electrocardiogram wave data; generating a component of the cardiac massage from the feature pattern; and removing the generated component from the original electrocardiogram wave data.

Preferably, identifying the first electrocardiogram wave includes: when a Fourier series expansion is expressed by the expression 3:

$$y(t) = a_0 + \sum_{i=1}^{\infty}\left(a_i\cos\frac{2\pi it}{T} + b_i\sin\frac{2\pi it}{T}\right)$$

and an approximate wave of the Fourier series expansion is expressed by the expression 4:

$$\hat{y}(t) = \alpha_0 + \sum_{i=1}^{M}\left(\alpha_i\cos\frac{2\pi it}{T} + \beta_i\sin\frac{2\pi it}{T}\right)$$

assuming that the obtained electrocardiogram wave data is a wave in which a fundamental wave component and a harmonic wave component overlap each other, making errors of $\hat{y}(t)$ and y(t) as small as possible by adjusting $\alpha=(\alpha_0, \alpha_1, \alpha_2, \alpha_3, \ldots)$ and $\beta=\beta_1, \beta_2, \beta_2, \ldots$ ); and searching $\alpha$ and $\beta$ to identify and extract the electrocardiogram wave data to be analyzed.

In addition, preferably, the method further includes storing plural feature patterns (referred to as registration feature patterns) in a storage unit in advance, and sequentially cross-checking the first electrocardiogram wave data with the registration feature patterns to determine the most similar registration feature pattern to the first electrocardiogram wave data.

In addition, preferably, the method further includes displaying on a display an electrocardiogram wave (second electrocardiogram wave) of which the component of the cardiac massage is removed.

According to a third aspect of the invention, there is provided a method of obtaining and analyzing electrocardiogram wave data, the method including: performing analog/digital conversion on an electrocardiogram wave obtained from a subject that is continuously subjected to a cardiac massage to obtain electrocardiogram wave data; identifying the electrocardiogram wave from the obtained electrocardiogram wave data; generating a component of the cardiac massage using a feature pattern including a feature when the cardiac massage has been performed with respect to the identified electrocardiogram wave data; and removing the generated component of the cardiac massage from the electrocardiogram wave data.

According to a fourth aspect of the invention, there is provided a computer-executable program for analyzing obtained electrocardiogram wave data, the program including instructions for implementing: means for identifying an electrocardiogram wave from the obtained electrocardiogram wave data; means for selecting a feature pattern including a feature when a cardiac massage has been performed with respect to the electrocardiogram wave data identified by the identification means; means for generating a component of the cardiac massage using the feature pattern selected by the means; and means for removing the component of the cardiac massage generated in the generation means, from the obtained electrocardiogram wave data.

According to the present invention, electrocardiogram wave data obtained by cardiac massage can be processed such that the component of the cardiac massage is removed while the cardiac massage is continuously performed. This therefore allows the electrocardiogram wave to which defibrillation must be applied to be identified at the time of cardiopulmonary resuscitation.

In addition, the electrocardiogram wave data can be continuously taken and analyzed without stopping the cardiac massage, so that the damage of the subject accompanying the stopping of the resuscitation can be reduced.

BRIEF DESCRIPTION OF THE DRAWINGS

FIG. 2 is a diagram illustrating constitutional blocks of an electrocardiogram wave processing system according to an embodiment of the invention;

DESCRIPTION OF THE PREFERRED EMBODIMENTS

The present inventors first collected an enormous amount of electrocardiogram wave data, and analyzed what processing was performed on the recorded electrocardiogram wave data and what features the recorded electrocardiogram wave data have. To perform the analysis, a frequency domain analysis and a time domain analysis were applied. And it was found that the electrocardiogram wave data during resuscitation was of a wave in which features of the electrocardiogram wave of the cardiac massage and the VF wave overlapped each other and these waves might be separated from each other. In addition, with respect to the wave recognition, it was found that the time domain analysis could be effectively used in combination with the frequency domain analysis, the electrocardiogram wave analysis, and the similarity determination of the analyzed results.

Based on the knowledge mentioned above, electrocardiogram wave data was collected during the cardiac massage, and an algorithm for removing a component of the cardiac massage from the electrocardiogram wave data was developed, which were then applied to an electrocardiogram wave processing system.

Hereinafter, an embodiment of the present invention will be described in detail with reference to accompanying drawings.

Figure 1:
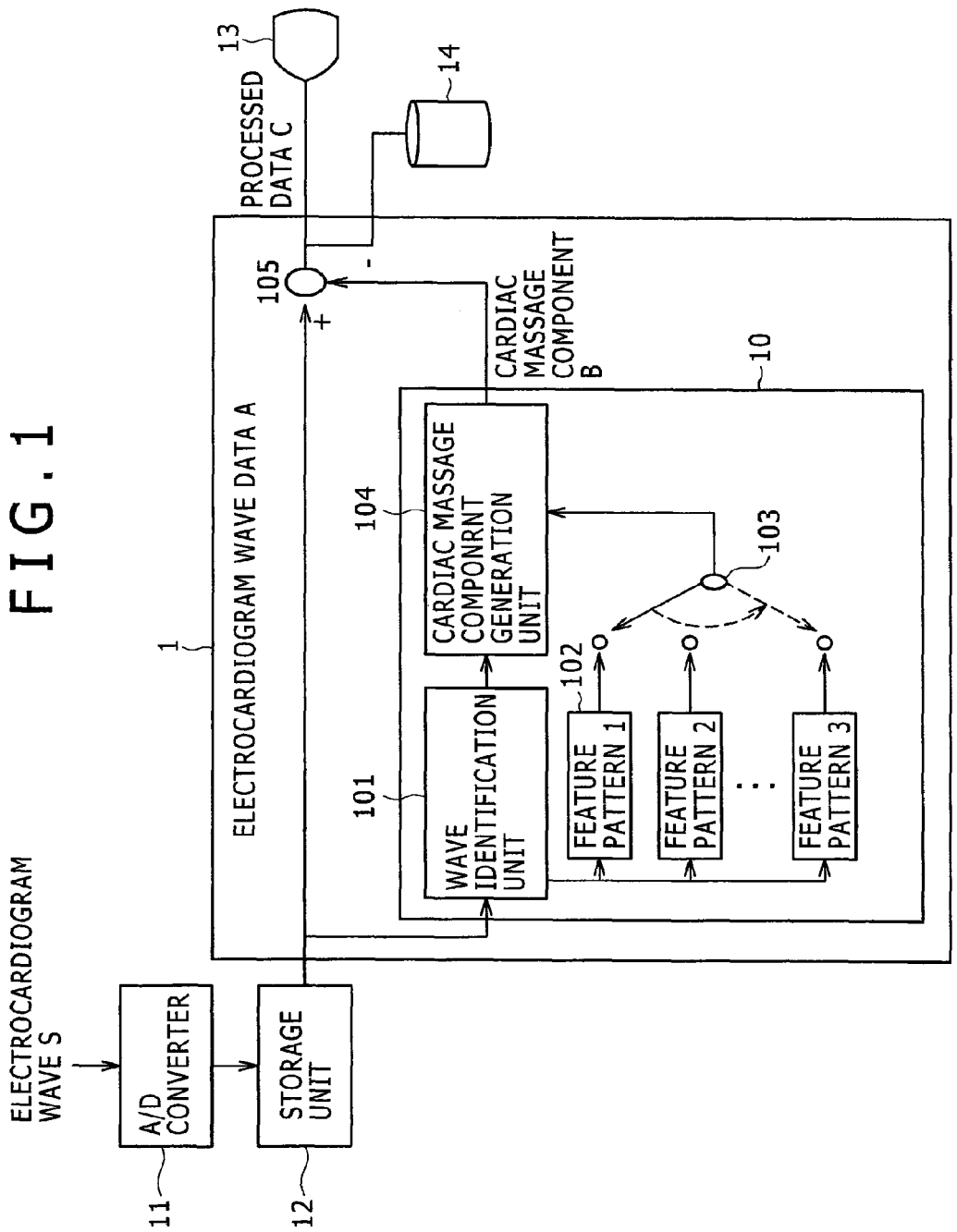
FIG. 1 is a block diagram illustrating the configuration of an electrocardiogram wave processing system according to an embodiment of the invention.

FIG. 1 illustrates the configuration of an electrocardiogram wave processing system according to an embodiment of the invention.

The electrocardiogram wave system includes an analog/digital (A/D) converter 11 that converts an electrocardiogram wave sensed by a sensor attached to the chest of a subject, a storage unit 12 such as a flash memory or a hard disk that stores the electrocardiogram wave data output from the A/D converter 11, a processing unit 1 that processes the electrocardiogram wave data read out from the storage unit 12, a display 13 that displays the electrocardiogram wave data C processed by the processing unit 1 as the electrocardiogram wave, and a storage unit 14 such as a hard disk that stores the processed electrocardiogram wave data C. In addition, the storage unit 14 may be the same as the storage unit 12 such as a hard disk. In addition, although not shown in the drawing, a filter of removing a high frequency noise may be disposed at a front end of the A/D converter 11 where the electrocardiogram wave is input.

When a cardiac massage is performed, the component of the performed cardiac massage is overlapped and included in the electrocardiogram wave S and the electrocardiogram wave data A. The processing unit 1 performs specific processing for removing the component of the cardiac massage from the electrocardiogram wave data A in accordance with the present invention.

The processing unit 1 has a cardiac massage estimating portion 10 that estimates the component of the cardiac massage of the electrocardiogram wave data A, and a subtracting portion 105 that removes the cardiac massage component B from the electrocardiogram wave data A.

The cardiac massage component estimating portion 10 has a wave identification unit 101, a selector 103, and a cardiac massage component generation unit 104. In addition, plural different feature patterns 102 are stored in the storage unit 12 in advance. The feature patterns 102 are n patterns configured to include distinctive patterns reflected on the electrocardiogram wave data using a normalization distribution, adjustable parameters, and statistically collected thresholds when the heat massage was performed.

The wave identification unit 101 analyzes what components compose the input electrocardiogram wave data A, and generates the identified wave. The selector 103 selects the feature pattern k that is the closest to the corresponding electrocardiogram wave data A identified by the wave identification unit 101 in combination with the feature pattern 102.

The cardiac massage component generation unit 104 generates the component B of the cardiac massage included in the selected feature pattern k. The subtractor 105 subtracts the cardiac massage component B from the input electrocardiogram wave data A to output processed data C (=A−B) that does not include the cardiac massage component.

Figure 5:
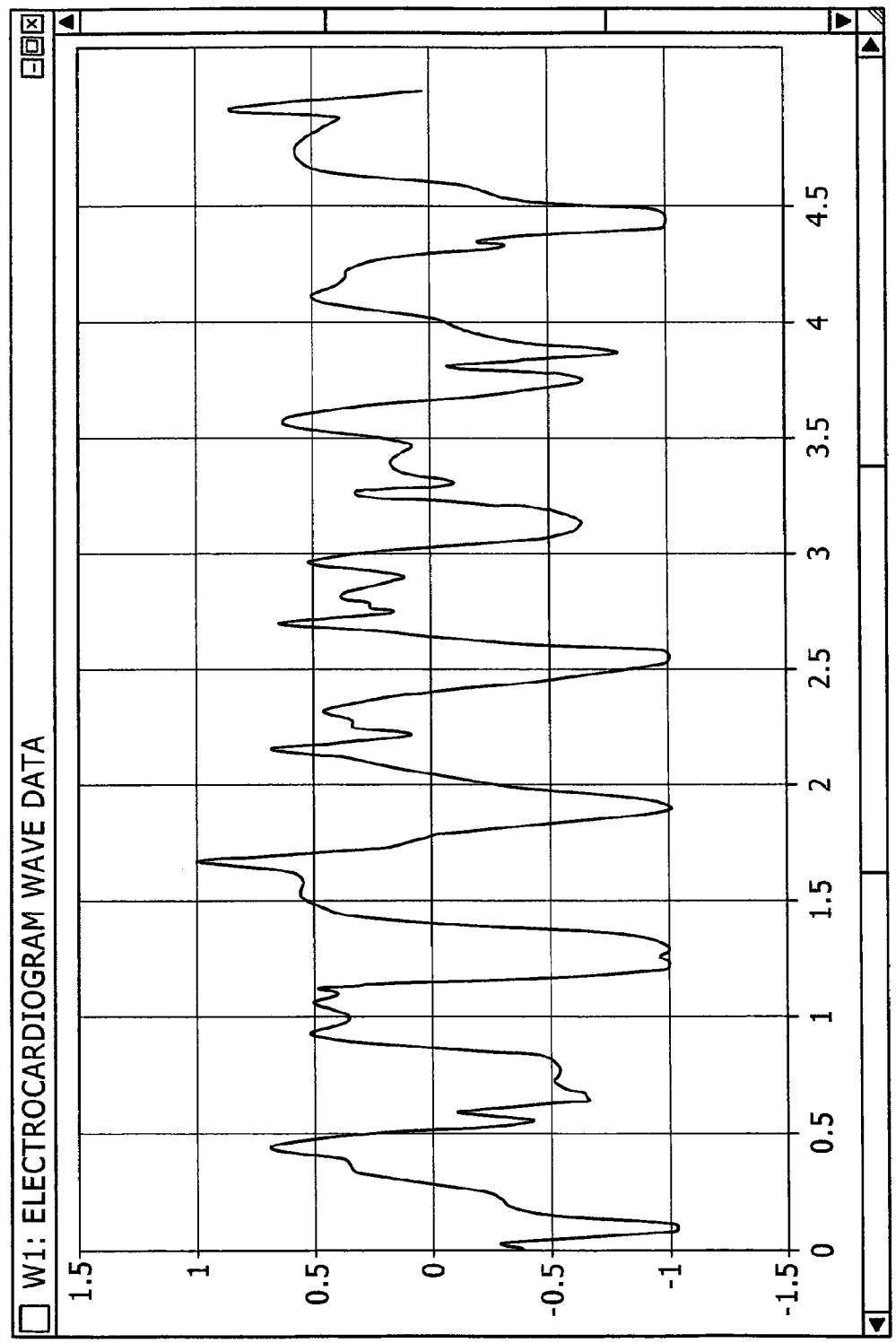
FIG. 5 is a diagram illustrating electrocardiogram waves according to an embodiment of the invention.
Figure 10:
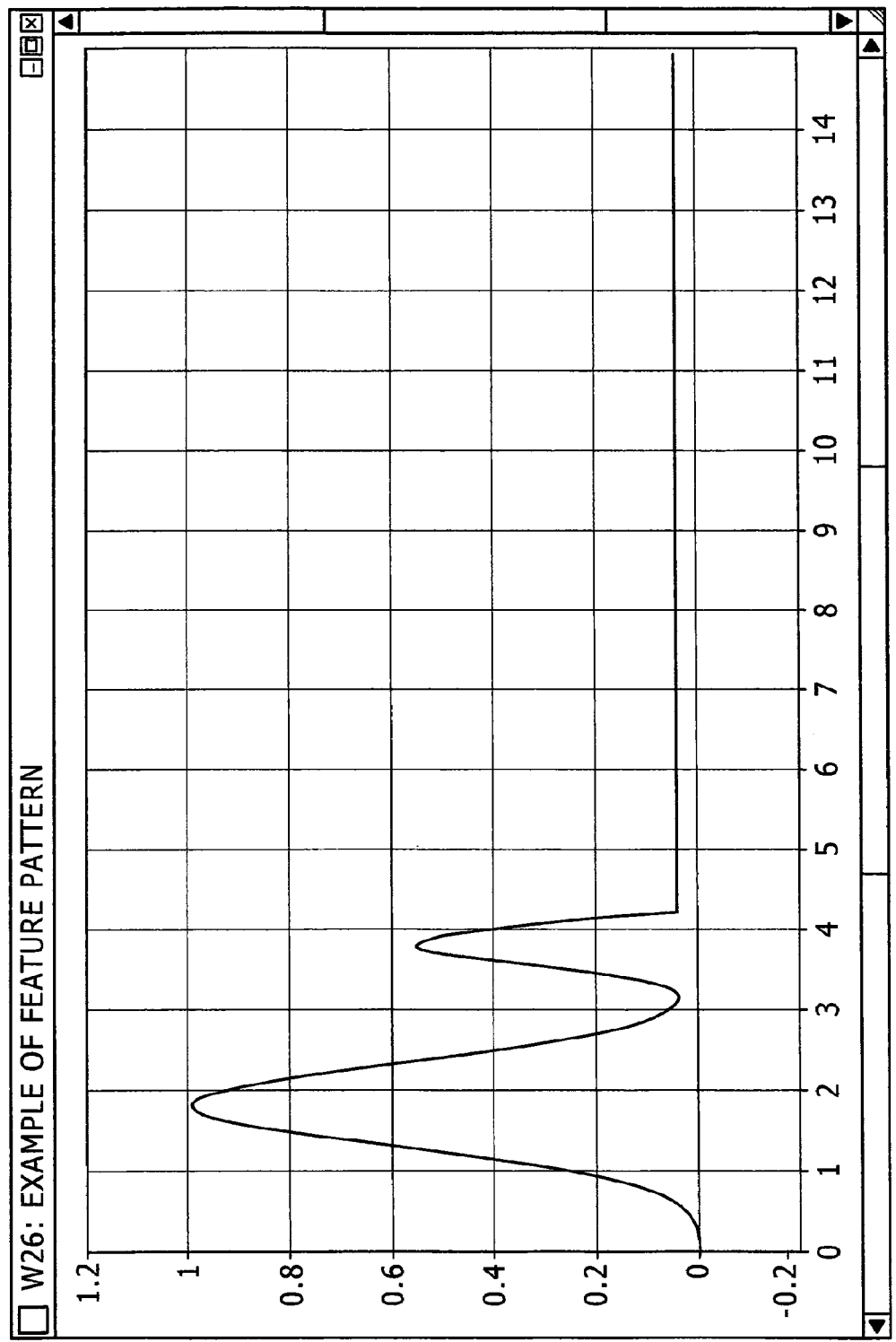
FIG. 10 is a diagram illustrating electrocardiogram waves according to another embodiment of the invention.
Figure 11:
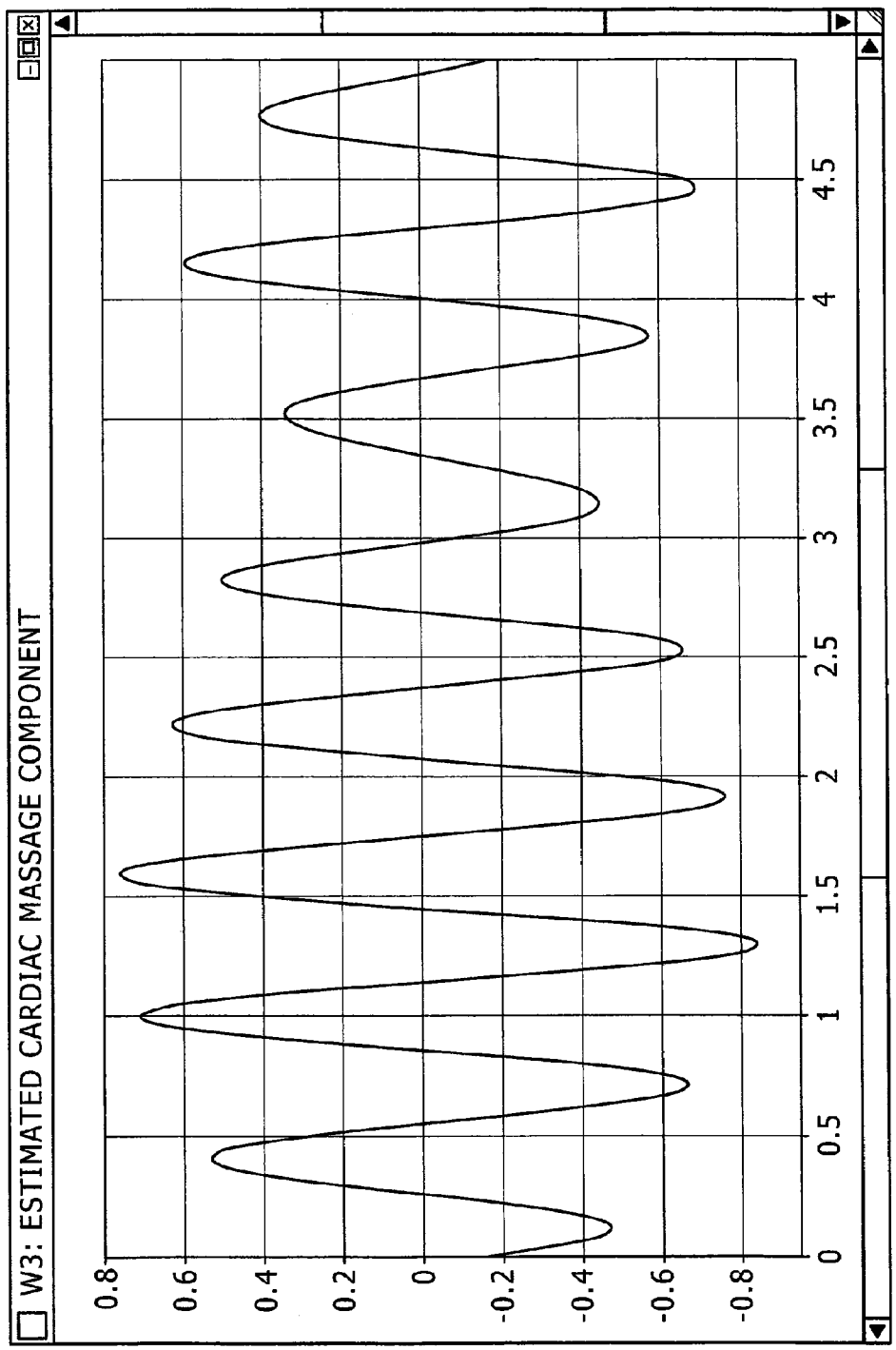
FIG. 11 is a diagram illustrating electrocardiogram waves according to another embodiment of the invention.
Figure 12:
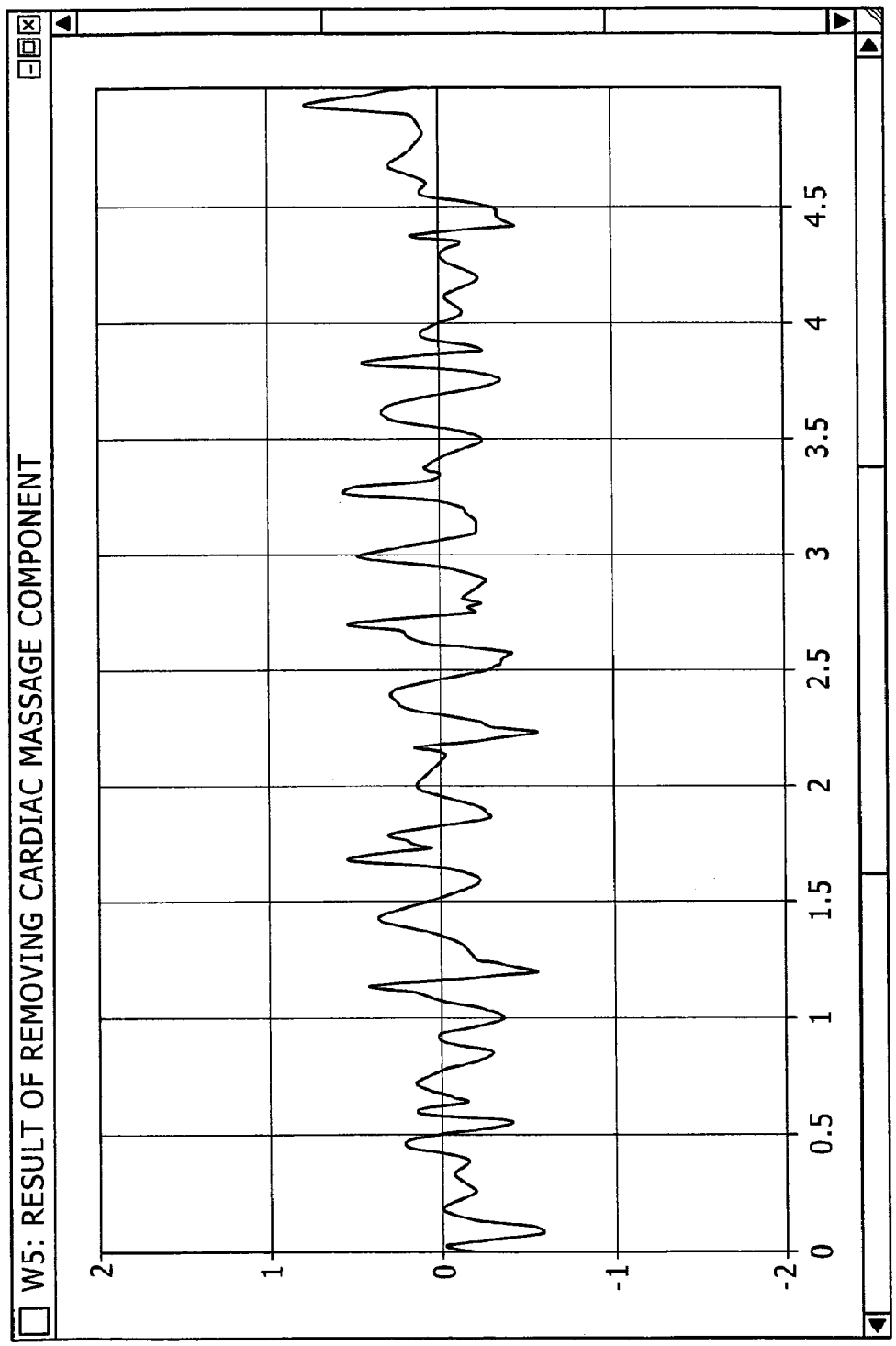
FIG. 12 is a diagram illustrating electrocardiogram waves according to another embodiment of the invention.
Figure 13:
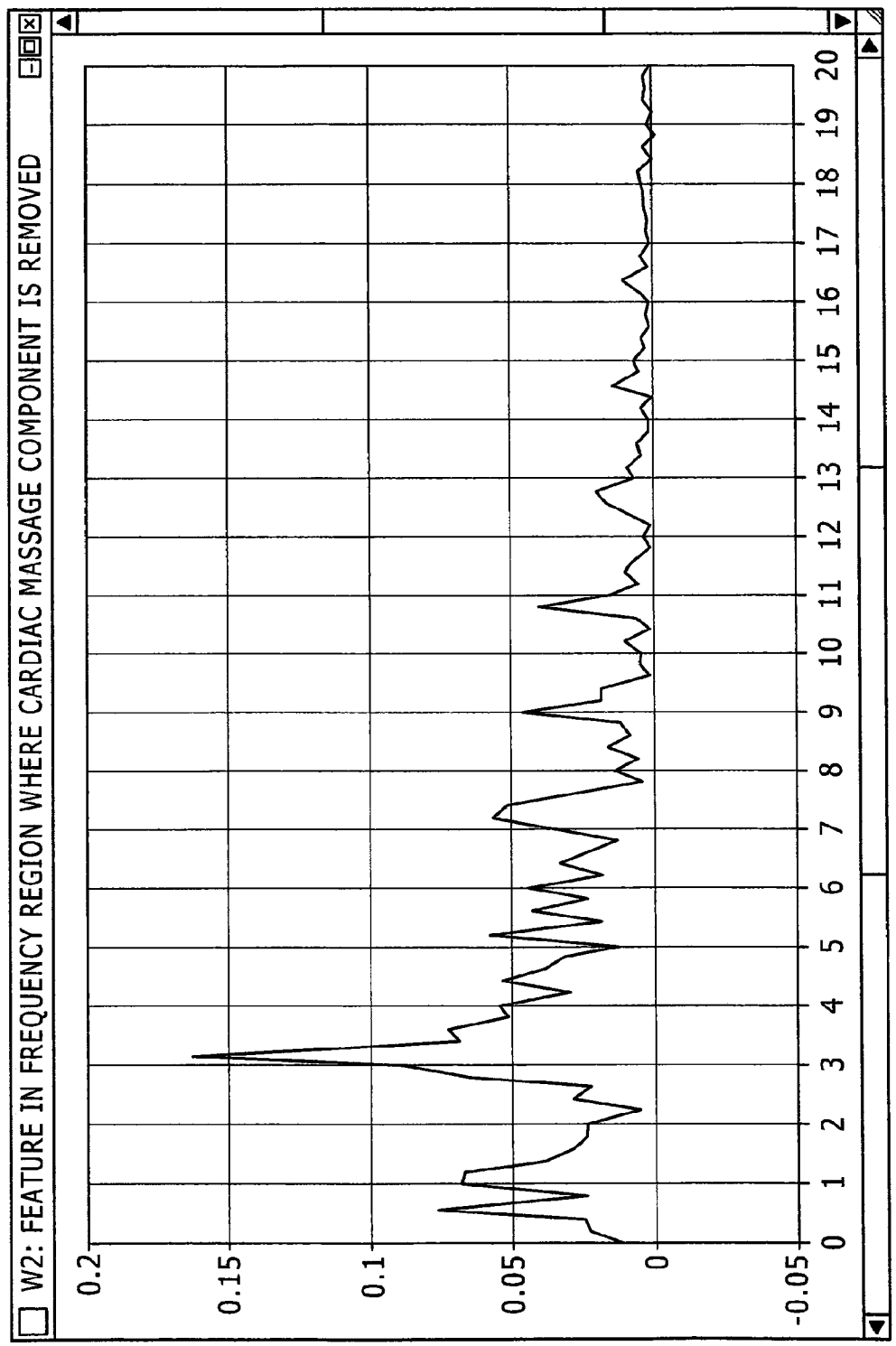
FIG. 13 is a diagram illustrating electrocardiogram waves according to another embodiment of the invention.
Figure 14C:
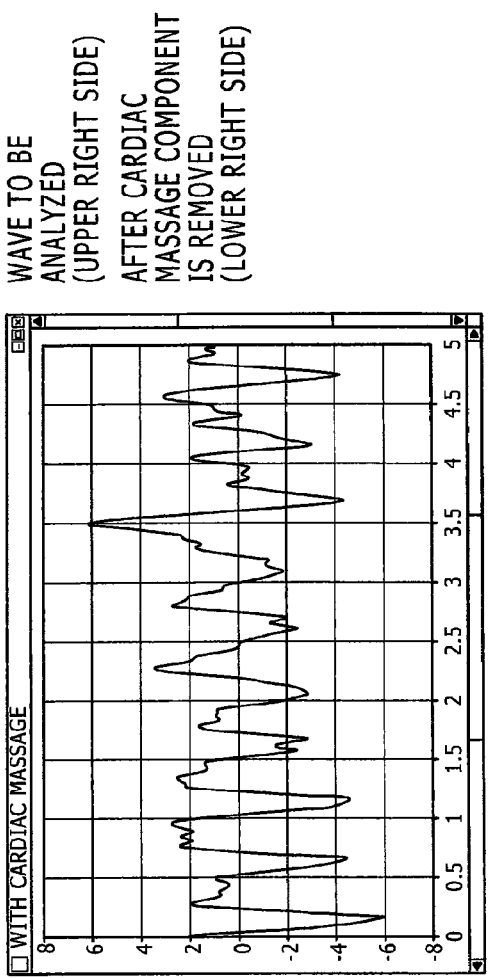
FIGS. 14A to 14D are diagrams illustrating electrocardiogram waves according to another embodiment of the invention.
Figure 14D:
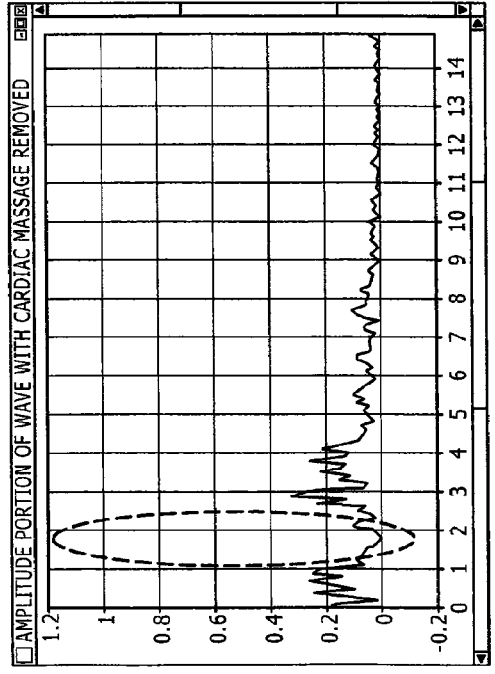
Figure 14A:
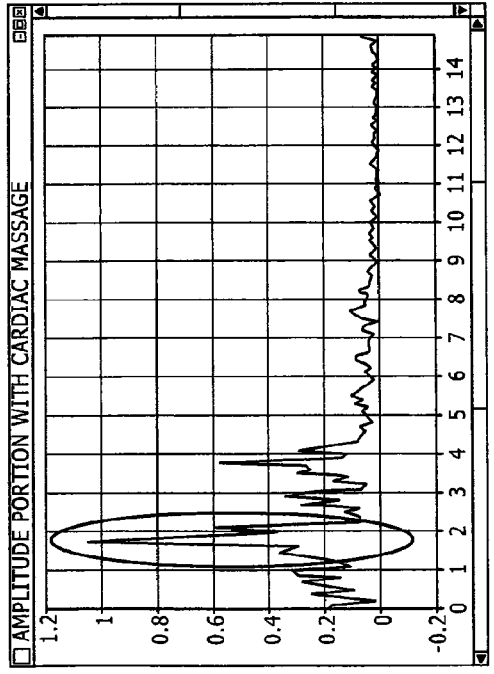
Figure 14B:
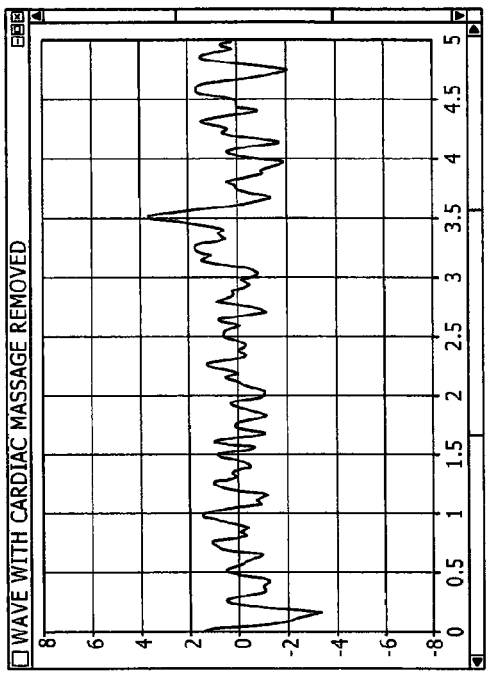

With respect to examples of the electrocardiogram waves, FIG. 5 illustrates an example of the electrocardiogram wave data A input to the wave identification unit 101, FIG. 10 illustrates an example of the feature pattern, FIG. 11 illustrates an example of the cardiac massage component B, FIGS. 12 and 14B illustrate the results that the cardiac massage component B was removed from the electrocardiogram wave data A. In addition, FIGS. 5, 12, and so forth illustrate the electrocardiogram wave data over time (a horizontal axis denotes a time axis and a vertical axis denotes an amplitude). In addition, FIG. 13 illustrates the frequency characteristic (relationship between the amplitude (vertical axis) and the frequency (horizontal axis)).

The time taken for obtaining the electrocardiogram wave data is 4 to 5 seconds, and the sampling rate is 1 kHz. Typically, the cardiac massage is performed at a rate of about 100 times/min, so that the wave B resulting from the cardiac massage is shown in a frequency range of about 1.5 to about 1.9 Hz.

[Explanation of Electrocardiogram Wave Recognition Algorithm]

At the moment of development on the algorithm of identifying the electrocardiogram wave, the present inventors have thought that identification of the electrocardiogram wave can be accomplished by mainly implementing processing of setting elements of the electrocardiogram wave to be identified, selecting the feature pattern, estimating the cardiac massage component, and removing the cardiac massage component from the electrocardiogram wave data. Therefore, the algorithms for implementing the respective processing will be described.

(1) Identification Algorithm of Electrocardiogram Wave (1.1) Basic Knowledge of Identifying Electrocardiogram Wave It is thought that the electrocardiogram wave is a periodical signal, which can be described as a collection of plural frequency components. Accordingly, the signal y(t) having the period T can be expanded by Fourier series as the expression 1 below:

$$y(t) = a_0 + \sum_{i=1}^{\infty} \left( a_i \cos \frac{2\pi i t}{T} + b_i \sin \frac{2\pi i t}{T} \right) \quad \text{expression 1}$$

$$= a_0 + \sum_{i=1}^{\infty} A_i \cos\left( \frac{2\pi i t}{T} - \theta_i \right)$$

where Ai and θi(i=1, ... ∞) denote amplitude and phase represented by the expression 2 below:

$$A_i = (a_i^2 + b_i^2)^{\frac{1}{2}} \quad \text{expression 2}$$

$$\theta_i = \tan^{-1} \frac{b_i}{a_i}$$

The electrocardiogram wave data A to be recorded is finite data, but it is not clear that the electrocardiogram wave data is periodical, and it can be assumed that (a) the wave to be analyzed is a periodic signal having the period T and (b) the wave to be analyzed is composed of a fundamental wave (sine wave or cosine wave) having its period as a fundamental frequency and a harmonic wave. Based on this assumption, constitutional elements of the wave can be analyzed using the Fourier series expansion of the expression 1. Its basic understanding is as follows. In addition, the parameters M and T of the expression 4 below denote the order of the harmonic wave component and the fundamental period, respectively.

(i) The wave as the subject can be represented by the collection of the fundamental wave component and the harmonic wave component as shown in the expression 3 below:

$$y(t) = a_0 + \sum_{i=1}^{\infty} \left( a_i \cos \frac{2\pi i t}{T} + b_i \sin \frac{2\pi i t}{T} \right) \quad \text{expression 3}$$

(ii) Similarly, an approximate wave can be represented by the expression 4.

$$\hat{y}(t) = \alpha_0 + \sum_{i=1}^{M} \left( \alpha_i \cos \frac{2\pi i t}{T} + \beta_i \sin \frac{2\pi i t}{T} \right) \quad \text{expression 4}$$

(iii) When the data length of y(t) is $T_L$ [sec] and the time interval is Δ[sec], N numerical (data length T=N×Δ[sec]) values are obtained by sampling, which is referred to as y(k)(k=1, 2, ... N).

$$y(k) = a_0 + \sum_{i=1}^{\infty} \left( a_i \cos \frac{2\pi i k \Delta}{T} + b_i \sin \frac{2\pi i k \Delta}{T} \right) \quad \text{expression 3-1}$$

$$(k = 1, 2, \ldots N)$$

(iv) ŷ(t) is the same as y(t), so that N sampled data indicate ŷ(k) (k=1, 2, ... N).

$$\hat{y}(k) = \alpha_0 + \sum_{i=1}^{M} \left( \alpha_i \cos \frac{2\pi i k \Delta}{T} + \beta_i \sin \frac{2\pi i k \Delta}{T} \right) \quad \text{expression 4-1}$$

$$(k = 1, 2, \ldots N)$$

By adjusting $\alpha=(\alpha_0, \alpha_1, \alpha_2, \alpha_3, \ldots \alpha_M)$ and $\beta=(\beta_1, \beta_2, \beta_3, \ldots \beta_M)$, errors of ŷ(k) and y(k) are made as small as possible.

In this case, $a_0$ and $\alpha_0$ denote direct current values (bias), which can be removed in advance by means of filtering. At this time, a becomes $\alpha=(\alpha_1, \alpha_2, \alpha_3, \ldots)$, however the same result can be obtained when $\alpha_0=0$ in the following description.

(1.2) Optimization for Identifying Electrocardiogram Wave

It is thought that errors of ŷ(k) and y(k) can be made as small as possible by adjusting the parameters $\alpha=(\alpha_0, \alpha_1, \alpha_2, \alpha_3, \ldots \alpha_M)$ and $\beta=(\beta_1, \beta_2, \beta_3, \ldots \beta_M)$ when the wave obtained by the identification is represented by ŷ(k)(k=1, ... N). In this case, M and T are design parameters, respectively.

Accordingly, it is thought that the objective function as shown in the expression 5 below can be minimized by the expression 6 using the parameters $\alpha=(\alpha_0, \alpha_1, \alpha_2, \alpha_3, \ldots \alpha_M)$ and $\beta=(\beta_1, \beta_2, \beta_3, \ldots \beta_M)$.

$$v(\alpha, \beta) = \sum_{k=1}^{N} (y(k) - \hat{y}(k))^2 \quad \text{expression 5}$$

Minimize $\{v(\alpha, \beta)\}$ $\quad$ expression 6
$\alpha, \beta$

This minimization is equivalent to searching for the parameters $\alpha=(\alpha_0, \alpha_1, \alpha_2, \alpha_3, \ldots \alpha_M)$ and $\beta=(\beta_1, \beta_2, \beta_3, \ldots \beta_M)$ meeting the condition below.

$$\frac{\partial v(\alpha, \beta)}{\partial \alpha} = 0 \quad \text{expression 7}$$

$$\frac{\partial v(\alpha, \beta)}{\partial \beta} = 0$$

As a method of searching for $\alpha=(\alpha_0, v_1, \alpha_2, \alpha_3, \ldots \alpha_M)$ and $\beta=(\beta_1, \beta_2, \beta_3, \ldots \beta_M)$ meeting the expression 7, a steepest descent method is employed. However, it is also possible to employ other optimization method or neutral network or the like to search for $\alpha=(\alpha_0, \alpha_1, \alpha_2, \alpha_3, \ldots \alpha_M)$ and $\beta=(\beta_1, \beta_2, \beta_3, \ldots \beta_M)$.

(2) Selection of Feature Pattern

According to an investigation of the present inventors, cases of the VF at the time that there was no cardiac massage and cases of the VF at the time that there was a cardiac massage were discriminated and analyzed with respect to electrocardiogram wave data A when the cardiac massage was performed and electrocardiogram wave data before and after the electrocardiogram wave data A, so that the following was found.

(i) There was a difference in cardiac massage wave due to the difference of the operators performing the cardiac massage.

(ii) Unlike the case of VF, the electrocardiogram wave data at the time of cardiac massage recorded before and after the electrocardiogram wave that is determined not to be VF while there is no cardiac massage, was occasionally shown to have the feature in a low-pass frequency.

(iii) The feature of the fundamental tuning wave was occasionally shown in the electrocardiogram wave data recorded during the cardiac massage.

Accordingly, plural feature patterns is stored in the storage unit in advance, which is in combination with the electrocardiogram wave data that was actually sensed to select the feature pattern having the highest similarity to the corresponding electrocardiogram wave data.

In this case, the feature patterns were generated based on the normalization distribution using adjustable parameters and thresholds determined by the statistical processing. That is, 1200 electrocardiogram wave data pieces were randomly extracted from the electrocardiogram wave data recorded before and after the electrocardiogram wave data that is likely to be the VF at the time that there is no cardiac massage, amplitude components obtained from identification of the extracted data were analyzed, and the determined thresholds were used, which were configured based on the normalization distribution. In this case, the average value in the normalization distribution was the adjustable parameter and the maximum peak value of the distribution was 1 (normalization). In addition, in order to calculate the similarity between the feature patterns and the actually obtained electrocardiogram wave data, for example, a method of calculating the distance therebetween was employed.

An algorithm of selecting the feature pattern using the distance calculation is as follows.

(i) As described above, the amplitude component of the electrocardiogram wave data can be obtained from the identification result. This is referred to as Ai(i=0, ... M), which is normalized. This is referred to as Ain.

(ii) The feature pattern also includes an amplitude component, so that this is referred to as Ak/i(k=1, 2, ... n). In this case, n is the number of the feature pattern.

(iii) A square of a difference between the normalized feature pattern Ain and each of the feature patterns Ak/i is calculated. That is, $$\varepsilon^k = \sum_{i=0}^{M}(A_{in} - A_i^k)^2 \qquad \text{expression 8}$$

($A_i^k$ is also referred to as Ak/i)

(iv) The pattern having the highest similarity, A*/i, that is, Ak/i having the minimum value of $\epsilon^k$ is selected.

(3) Estimation and Removal of Cardiac Massage Component

The cardiac massage component can be estimated using the identification result of the electrocardiogram wave data and the selected feature pattern.

This is obtained by multiplying the normalized selected feature pattern with a weighted value with respect to the identification result. That is, when the coefficients of the respective components obtained from the identification result are αi and βi and the selected feature pattern is A*/i, the estimated coefficients of the cardiac massage component are obtained by the expression 9.

$$O_{\alpha_i} = \alpha_i \times A_i^*$$

$$O_{\beta_i} = \beta_i \times A_i^* \qquad \text{expression 9:}$$

(In addition, $A_i^*$ is referred to as A*/i). Accordingly, the cardiac massage component Ô(t) is obtained by the expression 10.

$$\hat{O}(t) = \sum_{i=1}^{M}\left(O_{\alpha_i}\cos\frac{2\pi ik\Delta}{T} + O_{\beta_i}\sin\frac{2\pi ik\Delta}{T}\right) \qquad \text{expression 10}$$

When the cardiac massage component is removed from the electrocardiogram wave data, the wave of the expression 11 is obtained.

$$z(k) = \hat{y}(k) - \hat{O}(k) \qquad \text{expression 11:}$$

Next, specific embodiments of the electrocardiogram wave processing system will be described with reference to FIGS. 2 and 3.

In this electrocardiogram wave processing system, a computer such as a personal computer is employed to implement the processing of the electrocardiogram wave data A.

Figure 3:
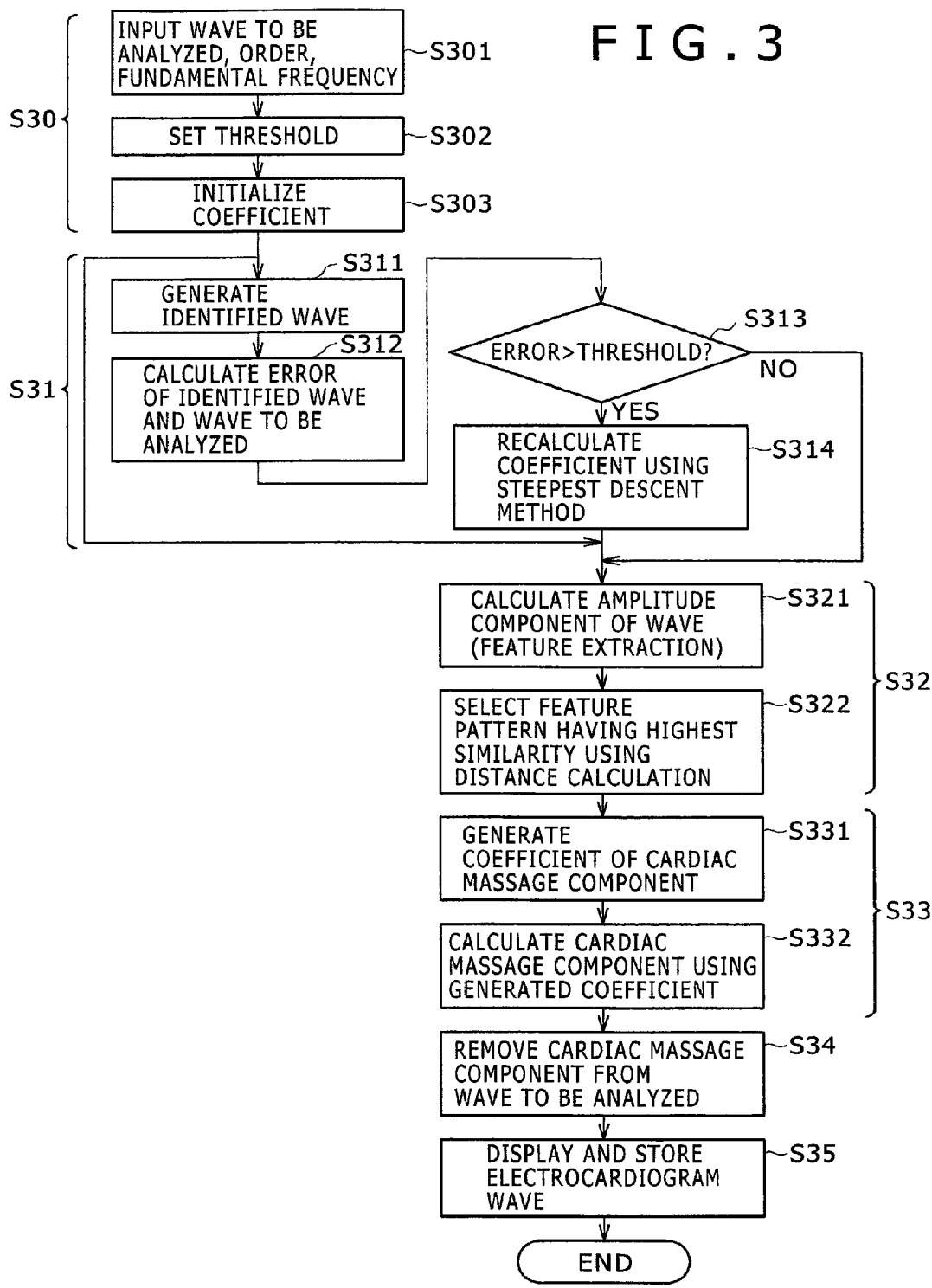
FIG. 3 is a flow chart illustrating processing operations of an electrocardiogram wave processing system according to an embodiment of the invention.

FIG. 2 illustrates an example of the configuration of the electrocardiogram wave processing system that executes a program for recognizing the electrocardiogram wave using a personal computer (PC), and FIG. 3 illustrates a flow chart of executing the program for processing the electrocardiogram wave data.

The electrocardiogram wave processing system includes a central processing unit CPU 20, a main memory 21, a storage unit 22 such as a hard disk, an input unit 23 such as a keyboard or a mouse, a display 24, and an adapter AD 25 for connection with an external apparatus, which are all connected to a common bus 29.

The CPU 20 executes the program 211 for processing the electrocardiogram wave data to implement an electrocardiogram wave identification function 201, a feature extraction function 202, a cardiac massage component estimation function 203, and a cardiac massage component removal function 204. The program 211 for processing the electrocardiogram wave data, and plural feature patterns 212 that are prepared in advance are stored in the memory 21. In addition, the feature patterns 212 may be stored in the storage unit 22 in advance and may be read out to the main memory 21 if required.

The adapter 25 is connected to a device of measuring the electrocardiogram wave via a predetermined interface. The device senses the electrocardiogram wave, converts the wave into digital data by means of A/D conversion, and transmits the converted electrocardiogram wave data to the adapter 25. The electrocardiogram wave data is temporarily stored in the main memory 21 or the storage unit 22.

Next, operations of processing the functions of the electrocardiogram wave processing system will be described with reference to the flow chart of FIG. 3.

In this flow chart, the step S30 is the function of initial processing, the step S31 is the function 201 of identifying the electrocardiogram wave, the step S32 is the function of extracting the feature, the step S33 is the function 203 of estimating the cardiac massage component, the step S34 is the function of implementing the function 204 of removing the cardiac massage component, and the step S35 is the function of displaying and storing the electrocardiogram wave of the processed result.

First, in the step S301 of the initial processing S30, coefficients of waves to be analyzed, orders of the harmonic component, and fundamental frequencies are input from the input unit 23. That is, an initial setting operation is performed for obtaining the electrocardiogram wave data of the subject to be analyzed from the adapter 25 and storing the data in the storage unit 22. This allows the order M and the fundamental period T of the harmonic components of the expressions 3 and 4 that was predefined to be set.

Similarly, in the step S302, the upper limit ($C \geq V(\alpha, \beta)$) of the expression 5 is set as a threshold C from the input unit 23. In addition, the order, the fundamental period, and the threshold of the harmonic component may be stored in the storage unit 22 in advance and may be read out to the memory 21. In addition, in the step S303, the coefficients of the expression 5, $\alpha$ and $\beta$, are input from the input unit 23 and are set.

In addition, prior to this initial processing, n feature patterns A1/I to AN/i (212) configured by the normalization distribution using the statistically collected thresholds and the adjustable parameters are stored in the storage unit 22 or the memory 21.

After the several coefficients mentioned above are initially set, in the step S311 of the electrocardiogram wave identification step S31, the identification wave $\hat{y}(k)$ is generated according to the expression 4. And in the step S312, errors of the identification wave of the expression 4 and the wave to be analyzed represented by the expression 3 are calculated from the expression 5.

In the step S313, the obtained error $V(\alpha, \beta)$ is compared with the threshold C that was initially set. When the error $V(\alpha, \beta)$ is greater than the threshold C, the steepest descent method is employed to recalculate the coefficients ($\alpha, \beta$), thereby repeating the steps S311 to S313. In the meantime, when the error is smaller than the threshold C, it is determined that the electrocardiogram wave of the subject is close to the approximate wave, so that the process proceeds to the feature extracting processing step S32. In addition, the number of repeating the steps S311 to S313 by means of coefficient recalculation is P, and when the error is still greater than the threshold C even in the step S313 reaching the repeating number P, the identification of the corresponding wave to be analyzed may be stopped to wait for an input of the next subject.

In the step S321 of the feature extraction processing S32, an amplitude component $A_i (i=0, \ldots M)$ is obtained for the identified electrocardiogram wave data.

In the step S322, the distance calculation is used to select the feature pattern having the highest similarity. This processing calculates $\epsilon^k$ according to the expression 8 to determine whether the calculated result is greater than the initially set threshold. When the calculated result is smaller than the threshold, it is determined that the corresponding Ak/i is the feature pattern having the highest similarity. In the meantime, when the calculated result is greater than the threshold, another feature pattern Ak+1/i is read out from the memory 21 to perform the calculation of the expression 8. This is repeatedly carried out until the maximum number n (the maximum number of the feature patterns), and when the calculated result is still greater than the threshold, it is determined that there is no optimal feature pattern, and the processing of the corresponding step S322 is terminated to wait for an input of the next electrocardiogram wave data. That is, the process waits for processing of the step S31.

When the feature pattern Ak/i having the highest similarity is selected with this processing, the process proceeds to the next step S33 of generating the massage component.

In the step S331 of the step S33 of generating the cardiac massage component, coefficients $O_{\alpha i}$ and $O_{\beta i}$ of the cardiac massage components are obtained from the expression 9. In addition, in the step S332, the cardiac massage component $\hat{O}$ is calculated from the expression 10.

The process then proceeds to the step S34 of removing the cardiac massage component, so that the cardiac massage component $\hat{O}(k)$ is removed from the initial electrocardiogram wave data $\hat{y}(k)$ according to the expression 11.

In the step S35, the electrocardiogram wave (processed result wave) in which the cardiac massage component is removed is displayed on the display 24 and is stored in the storage unit 22, so that the processing of recognizing one electrocardiogram wave is completed. In addition, when the next electrocardiogram wave is input to this processing system, the above-described processing is performed on the next electrocardiogram wave. The doctor may see the wave in which the cardiac massage component is removed, which is displayed on the display 24, and determines whether defibrillation must be performed.

Next, exemplary waves that are processed by the detection or processing device 20 or displayed on the display 24 in each processing step will be illustrated.

FIG. 5 illustrates an example of the electrocardiogram wave data A input to the electrocardiogram wave processing system of FIG. 1 or FIG. 2. This wave data is input to the wave identification unit 101 (or the electrocardiogram wave identification function 201). The horizontal and vertical axes denote the time t and the voltage value of the wave, respectively.

Figure 6:
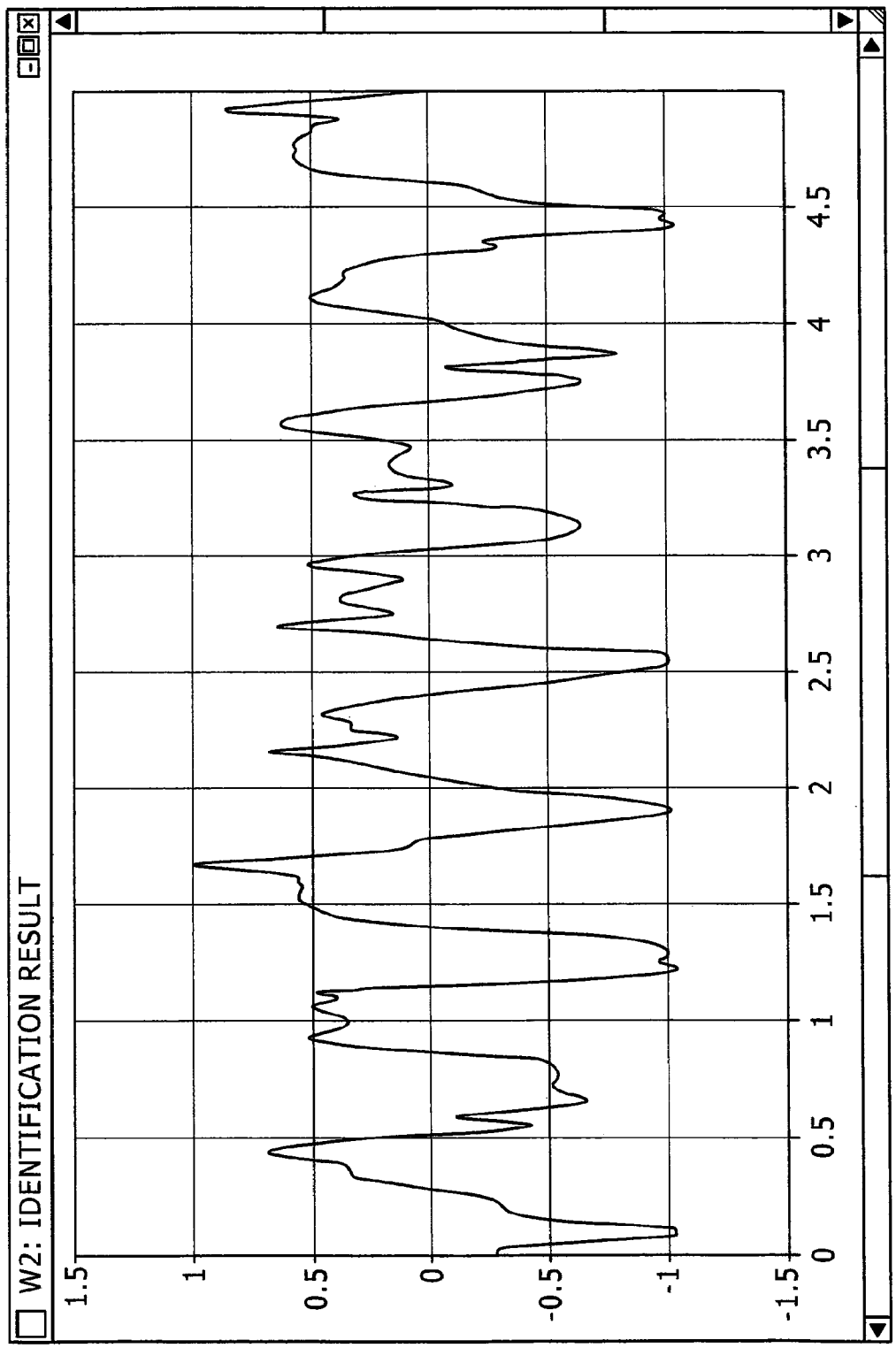
FIG. 6 is a diagram illustrating electrocardiogram waves according to another embodiment of the invention.

FIG. 6 illustrates the wave output from the wave identification unit 101 (or the electrocardiogram wave identification function 201).

Figure 7:
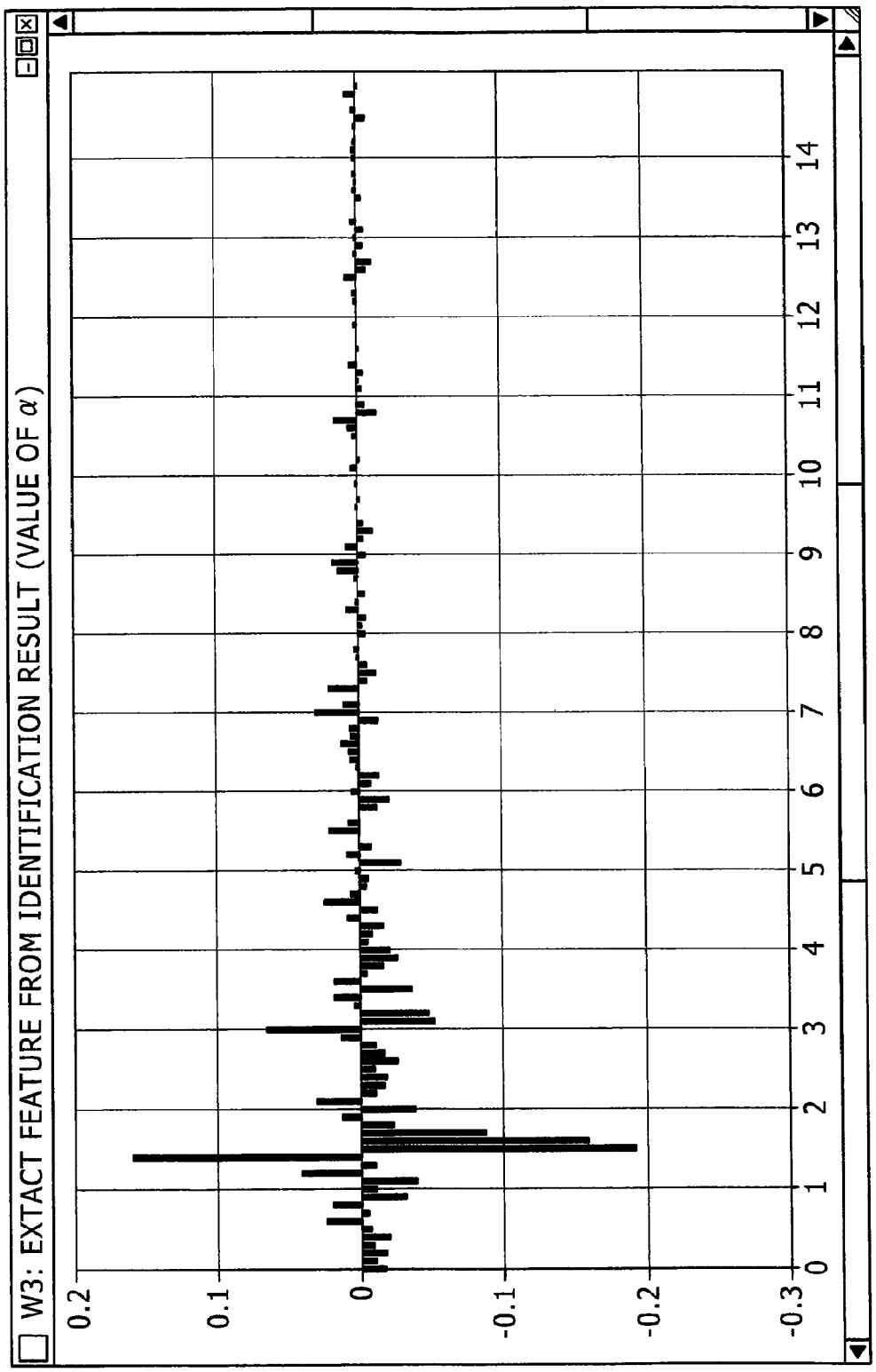
FIG. 7 is a diagram illustrating electrocardiogram waves according to another embodiment of the invention.
Figure 8:
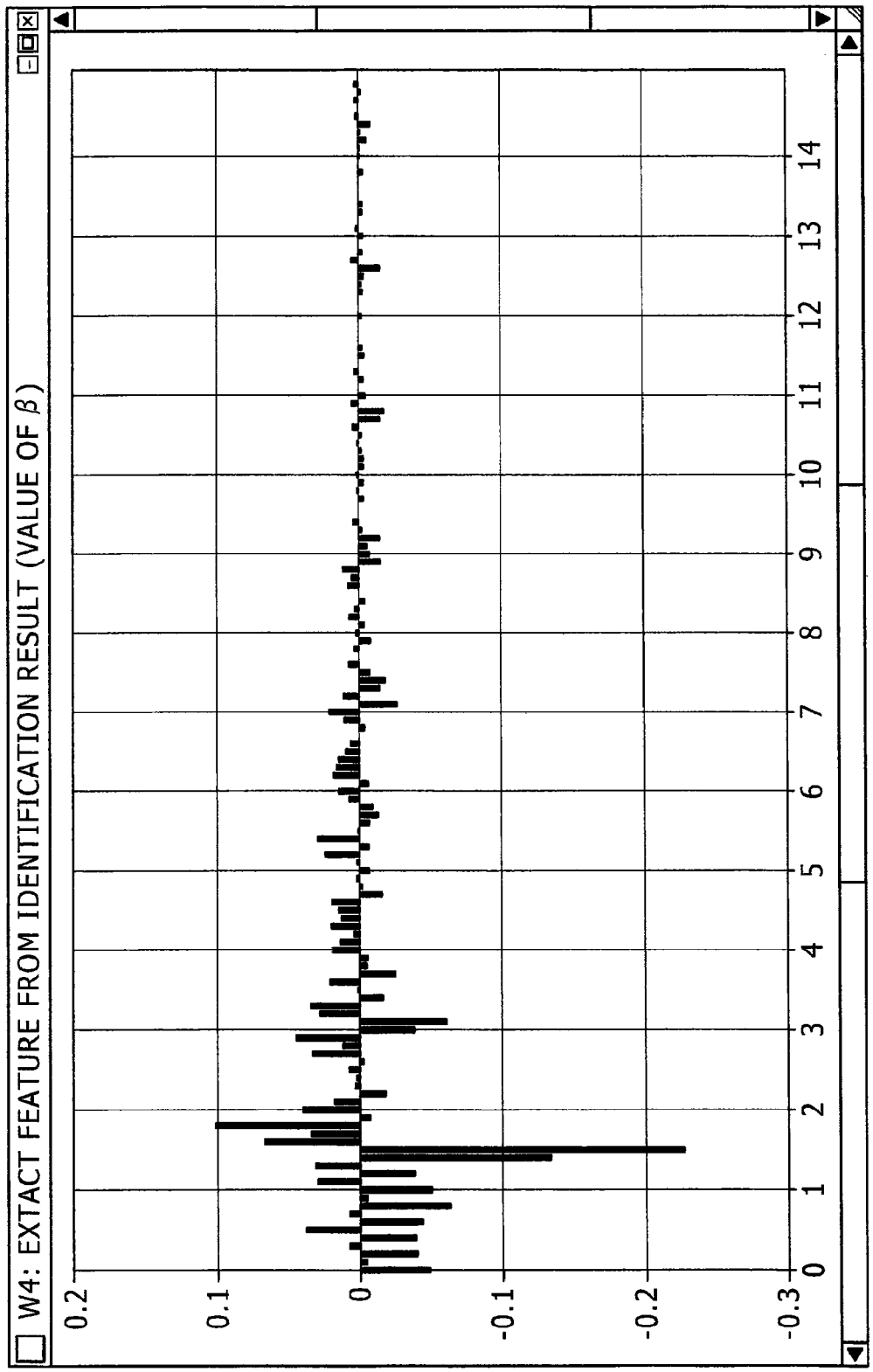
FIG. 8 is a diagram illustrating electrocardiogram waves according to another embodiment of the invention.

FIGS. 7 and 8 illustrate coefficients $\alpha$ and $\beta$ obtained by the expression 5 from the wave identification result. The horizontal and vertical axes denote the time t and the voltage value, respectively.

Figure 9:
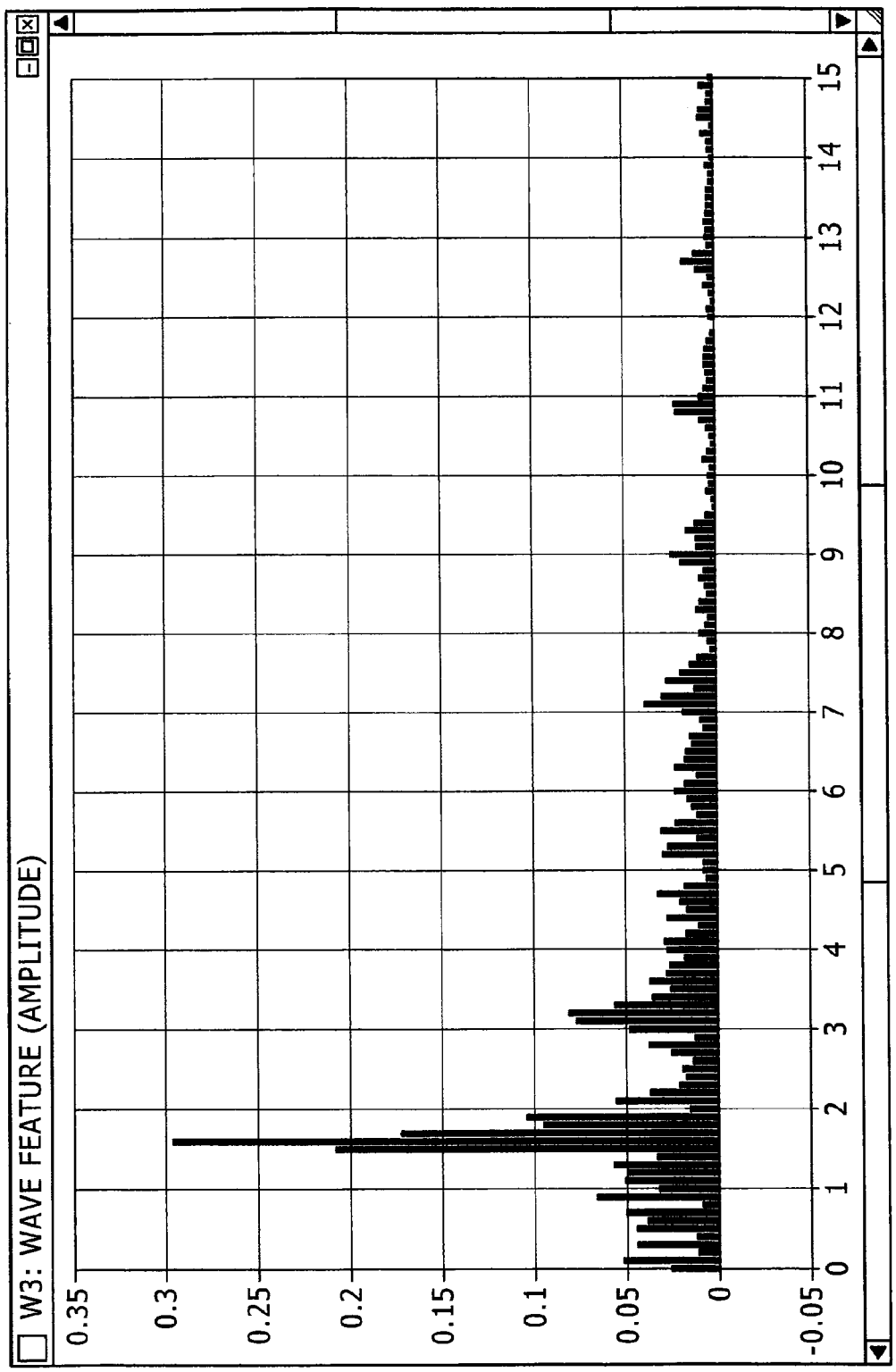
FIG. 9 is a diagram illustrating electrocardiogram waves according to another embodiment of the invention.

FIG. 9 illustrates an example of the feature resulting from the identified wave, and the horizontal and vertical axes denote the time t and the amplitude, respectively. The wave having a greater amplitude in the frequency range of 1.5 to 1.9 Hz (the range of about 1.5 to 1.9 Hz in the horizontal axis of FIG. 9) indicates the cardiac massage component. FIG. 9 illustrates the amplitude component of the wave calculated using coefficients $\alpha$ and $\beta$ and obtained from the expression 5 from the result of the identified wave.

FIG. 10 illustrates an example of n feature patterns configured by the normalization distribution using the statistically collected thresholds and the adjustable parameters. The horizontal and vertical axes denote the frequency and the amplitude, respectively.

FIG. 11 illustrates the cardiac massage component estimated by the expression 10. The horizontal and vertical axes denote the time t and the voltage value of the wave, respectively.

FIG. 12 illustrates the wave in which the cardiac massage component shown in FIG. 11 is removed from the electrocardiogram wave of FIG. 5. The horizontal and vertical axes denote the time t and the voltage value, respectively.

FIG. 13 illustrates the wave (frequency feature wave) in which the cardiac massage component is removed from the electrocardiogram wave of FIG. 10. The horizontal and vertical axes denote the frequency and the amplitude, respectively. It can be seen that the estimated cardiac massage component is removed.

In summary, an example of the recognized electrocardiogram wave data becomes present as shown in FIGS. 14A to 14D. Right waves 14C and 14D indicate the electrocardiogram waves to be analyzed, and left waves 14A and 14B indicate the frequency feature waves. In addition, upper waves 14A and 14C indicate the waves before the cardiac massage component is removed, and lower waves 14B and 14D indicate waves after the cardiac massage component is removed. The wave of the portion surrounded by the solid line in 14A corresponds to the main component resulting from the heat massage. When the cardiac massage is removed, it becomes the wave as shown in the dotted line in 14B.

Figure 4:
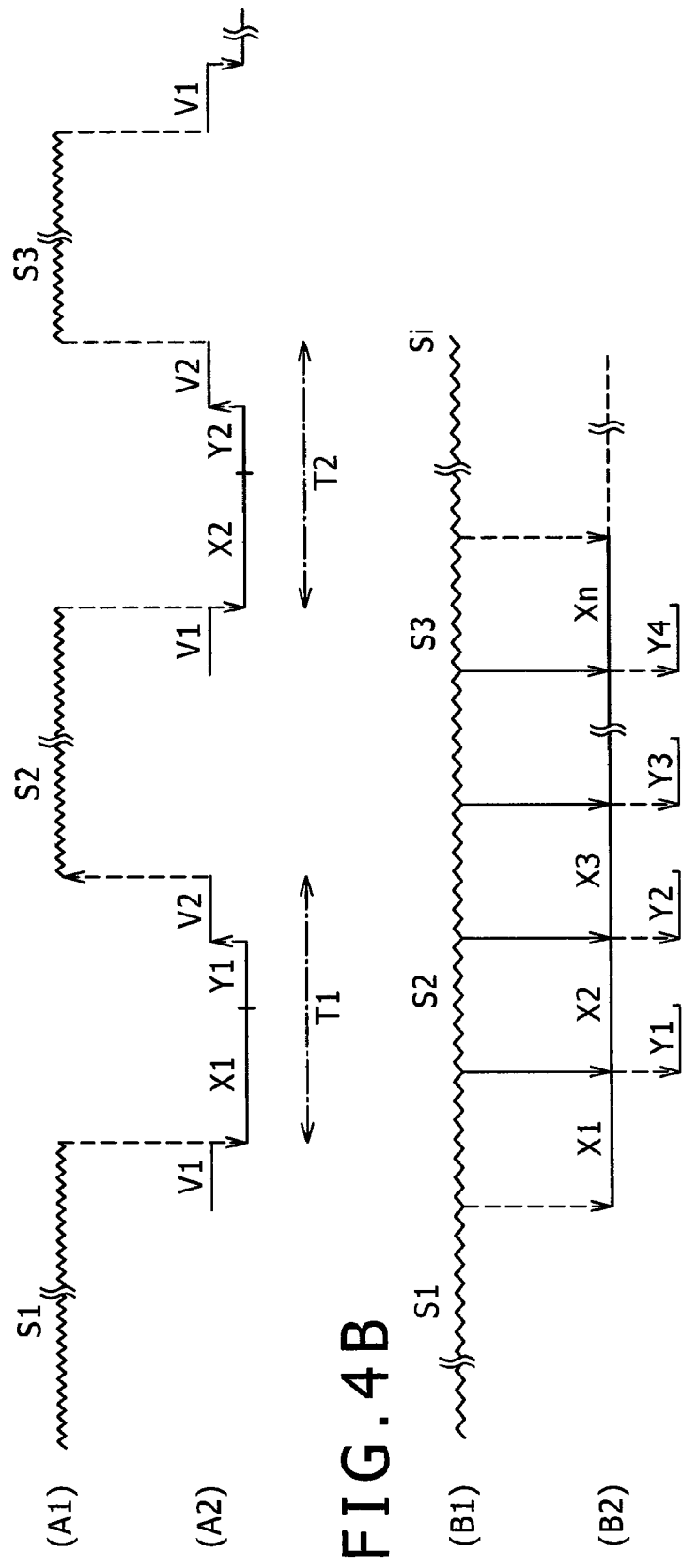
FIGS. 4A and 4B are diagrams illustrating the effect of an electrocardiogram wave processing system according to an embodiment of the invention.

FIGS. 4A and 4B are diagrams for explaining an effect of the present embodiment.

FIG. 4A indicates the case where the conventional semi-automatic defibrillation device is used, and FIG. 4B indicates the case where the electrocardiogram wave process of the present embodiment is applied.

Referring to FIG. 4A, S1, S2, and so on denote the processes of performing the cardiac massage. Typically, the duration of the cardiac massage Si is 120 seconds. After that, when an announcement V1 indicating "please hands off" occurs for about 2 seconds, the operator stops performing the cardiac massage. After that, detection X1 of the electrocardiogram wave is performed for about 4 to 5 seconds, and analysis Y1 of the detected electrocardiogram wave is performed for about 2 seconds. After that, when an announcement V2 indicating "please perform the cardiac massage again" occurs for about 9 seconds, the cardiac massage S2 is performed again for 120 seconds. This is repeated.

In this case, T1 (=X1+Y1+V2) becomes about 16 seconds. Typically, the cardiac massage is performed at this duration. However, when the cardiac massage must be stopped and the defibrillation must be performed, the duration may actually exceed one minute, because of the description for the apparatus status of the semiautomatic defibrillation apparatus being charged or a voice announcement for performing the defibrillation, thereby possibly causing more damage to the brain of the subject.

To deal with this, according to the present embodiment, the electrocardiogram wave is detected (X1) and is analyzed (Y1) while the cardiac massage is continuously performed without being stopped as shown in (B1). Actually, the detected electrocardiogram wave data is subjected to A/D conversion and is stored in the storage unit, which is then read out for analysis. The analysis process (Y1) is to remove the component of the cardiac massage from the obtained electrocardiogram wave. This time T (=X1+Y1) is about 6 seconds.

The doctor (or emergency life guard) can determine whether the defibrillation is required while listening to the determination result of the defibrillation or monitoring the wave in which the cardiac massage component is removed. In addition, the electrocardiogram wave can be taken and analyzed without stopping the cardiac massage, so that it is possible to avoid an adverse effect resulting from the stopped cardiac massage on the cardiopulmonary resuscitation.

In this way, the electrocardiogram wave processing system according to the present embodiment can advantageously provide information for determining whether the defibrillation needs to be applied by analyzing the electrocardiogram wave using specific processing.

In addition, the electrocardiogram wave processing system may be applied to the defibrillation apparatus in other applications. An automated or semi-automated external defibrillator (AED) is an apparatus, which is driven by a battery and performs electrical defibrillation by means of the electrode attached to the patient. For example, the electrocardiogram wave processing system shown in FIG. 1 or FIG. 2 may be applied to an AED having an electrocardiogram monitor, so that the AED can display on the monitor the result of the electrocardiogram wave processed according to the present embodiment.

In the meantime, well-known AEDs may have a voice unit without the electrocardiogram monitor. In this kind of AED, the voice unit notifies the operator such as the emergency life guard of whether the defibrillation must be performed. Accordingly, in this AED, for example, the structure in FIG. 2 of which the display 13 is removed is applied thereto, and predetermined patterns of the electrocardiogram waves where the defibrillation must be applied are stored in the storage unit in advance. It is determined whether the defibrillation must be applied by cross-checking the electrocardiogram wave output from the removal unit 205 with the predetermined patterns that are prepared in the storage unit in advance. Upon determination that the defibrillation must be applied, the operator is notified by voice means. In addition, an alarming unit such as an alarming display may be employed instead of or in addition to the voice means. When the alarm from the alarming unit is present, the operator may perform the defibrillation.

Terms or symbols used in the embodiments above are exemplary. Others may be employed sometimes, however, they must be determined in view of the gist of the present invention. In addition, the present invention may be variously modified without being limited to the embodiments above.

What is claimed is:

1. A system of analyzing electrocardiogram wave data obtained from a subject, comprising:
    a wave identification unit that identifies a first electrocardiogram wave from the obtained electrocardiogram wave data;
    a feature selection unit that selects a feature pattern including a feature when a cardiac massage has been performed with respect to the electrocardiogram wave data of the first electrocardiogram wave identified by the wave identification unit;
    a generation unit that generates a component of the cardiac massage using the feature pattern selected by the feature selection unit; and
    a removal unit that removes, from the obtained electrocardiogram wave data, the component of the cardiac massage generated by the generation unit;
    wherein said wave identification unit executes the following expressions to identify the first electrocardiogram wave:
    a Fourier series expansion expressed by the expression:

$$y(t) = a_0 + \sum_{i=1}^{\infty} \left( a_i \cos \frac{2\pi i t}{T} + b_i \sin \frac{2\pi i t}{T} \right)$$

and an approximate wave of the Fourier series expansion expressed by the expression:

$$\hat{y}(t) = \alpha_0 + \sum_{i=1}^{M} \left( \alpha_i \cos \frac{2\pi i t}{T} + \beta_i \sin \frac{2\pi i t}{T} \right),$$

and assuming that the obtained electrocardiogram wave data describes a wave in which a fundamental wave component and a harmonic wave component overlap each other, errors of $\hat{y}(t)$ and $y(t)$ are made to be as small as possible by adjusting $\alpha=(\alpha 0, \alpha 1, \alpha 2, \alpha 3, \ldots)$ and β=(β1, β2, β3, . . . ), thereby searching α and β to identify and extract the electrocardiogram wave data to be analyzed.

2. The system according to claim 1, further comprising:
a storage unit that stores a plurality of different registration feature patterns in advance,
wherein the feature selection unit refers to the registration feature patterns stored in the storage unit to select the registration feature pattern that is the most similar to the feature pattern included in the electrocardiogram wave data of the first electrocardiogram wave identified by the wave identification unit.

3. The system according to claim 2, further comprising:
a determination unit that determines whether defibrillation needs to be applied to the subject by cross-checking an electrocardiogram wave output from the removal unit with predetermined wave information already prepared in the storage unit; and
an alarm unit that raises an alarm by sound or display upon determination of the determination unit that the defibrillation needs to be applied to the subject.

4. The system according to claim 1, wherein the generation unit multiplies a normalized value of the selected feature pattern by a weighted value with respect to the first electrocardiogram wave identified by the wave identification unit.

5. The system according to claim 1, wherein the removal unit mainly removes, from the electrocardiogram wave data, the component of the cardiac massage of which the electrocardiogram wave data has an amplitude component ranging from 1.5 Hz to 1.9 Hz.

6. The system according to claim 1, further comprising:
a display that displays a second electrocardiogram wave output from the removal unit of which the component of the cardiac massage is removed.

7. The system according to claim 1, further comprising:
a processing unit that executes a computer program which implements each function of the wave identification unit, the feature selection unit, the generation unit, and the removal unit.

8. A method of obtaining and analyzing electrocardiogram wave data using a processing apparatus, comprising:
identifying a first electrocardiogram wave when a cardiac massage has been performed from the obtained electrocardiogram wave data;
selecting a feature pattern from the electrocardiogram wave data of the identified first electrocardiogram wave;
generating a component of the cardiac massage from the feature pattern; and
removing the generated component from the obtained electrocardiogram wave data;
wherein the following expressions are executed when identifying the first electrocardiogram wave:
a Fourier series expansion expressed by the expression:

$$y(t) = a_0 + \sum_{i=1}^{\infty}\left(a_i \cos\frac{2\pi i t}{T} + b_i \sin\frac{2\pi i t}{T}\right)$$

and an approximate wave of the Fourier series expansion expressed by the expression:

$$\hat{y}(t) = \alpha_0 + \sum_{i=1}^{M}\left(\alpha_i \cos\frac{2\pi i t}{T} + \beta_i \sin\frac{2\pi i t}{T}\right),$$

assuming that the obtained electrocardiogram wave data describes a wave in which a fundamental wave component and a harmonic wave component overlap each other, making errors of ŷ(t) and y(t) as small as possible by adjusting α=(α0, α1, α2, α3, . . . ) and β=(β1, β2, β3, . . . ); and
searching α and β to identify and extract the electrocardiogram wave data to be analyzed.

9. The method according to claim 8, further comprising:
storing a plurality of registration feature patterns in a storage unit in advance; and
sequentially cross-checking the electrocardiogram wave data of the first electrocardiogram wave with the registration feature patterns to determine the most similar registration feature pattern included in the electrocardiogram wave data of the first electrocardiogram wave.

10. The method according to claim 8, further comprising:
displaying a second electrocardiogram wave of which the component of the cardiac massage is removed.

11. A non-transitory computer readable medium comprising instructions for executing a method of analyzing obtained electrocardiogram wave data, the method comprising the steps of:
identifying an electrocardiogram wave from the obtained electrocardiogram wave data;
selecting a feature pattern including a feature when a cardiac massage has been performed with respect to the electrocardiogram wave data of the identified electrocardiogram wave;
generating a component of the cardiac massage from the selected feature pattern; and
removing the generated component of the cardiac massage from the obtained electrocardiogram wave data;
wherein the following expressions are executed in identifying the electrocardiogram wave:
a Fourier series expansion expressed by the expression:

$$y(t) = a_0 + \sum_{i=1}^{\infty}\left(a_i \cos\frac{2\pi i t}{T} + b_i \sin\frac{2\pi i t}{T}\right)$$

and an approximate wave of the Fourier series expansion expressed by the expression:

$$\hat{y}(t) = \alpha_0 + \sum_{i=1}^{M}\left(\alpha_i \cos\frac{2\pi i t}{T} + \beta_i \sin\frac{2\pi i t}{T}\right),$$

and assuming that the obtained electrocardiogram wave data describes a wave in which a fundamental wave component and a harmonic wave component overlap each other, errors of ŷ(t) and y(t) are made to be as small as possible by adjusting α=(α0, α1, α2, α3, . . . ) and β=(β1, β2, β3, . . . ), thereby searching α and β to identify and extract the electrocardiogram wave data to be analyzed.

* * * * *